United States Patent [19]

Merijanian

[11] Patent Number: 4,533,782
[45] Date of Patent: Aug. 6, 1985

[54] METHOD AND CATALYST FOR POLYMERIZING A CATIONIC POLYMERIZABLE MONOMER

[75] Inventor: Aspet V. Merijanian, Middlebury, Conn.

[73] Assignee: Uniroyal, Inc., Middlebury, Conn.

[21] Appl. No.: 530,334

[22] Filed: Sep. 8, 1983

[51] Int. Cl.³ ................................................ C07C 2/02
[52] U.S. Cl. .................... 585/520; 585/521; 585/522
[58] Field of Search .................... 585/520, 521, 522

[56] References Cited
U.S. PATENT DOCUMENTS
4,041,098 8/1977 Loveless ........................... 585/521

Primary Examiner—Curtis R. Davis
Attorney, Agent, or Firm—John A. Shedden

[57] ABSTRACT

Disclosed is a process for polymerizing cationically polymerizable monomers comprising:
(A) providing a solution containing an activated catalyst, said catalyst comprising
  (a) an aluminum compound having the formula $R_nAlX_{3-n}$, wherein n is an integer from 0 to 3; R is $C_1$-$C_{12}$ alkyl, $C_7$-$C_9$ aralkyl, $C_7$-$C_{18}$ alkaryl or $C_6$-$C_{10}$ aryl; and X is Cl, Br or I; and
  (b) (1) a compound having the formula R'X, wherein X is Cl, Br or I and R' is $C_1$-$C_{24}$ alkyl, $C_3$-$C_{20}$ alkenyl, $C_5$-$C_9$ bridged or non-bridged cycloalkyl or cycloalkenyl, $C_7$-$C_9$ aralkyl or (2) a hydrocarbon polymer carrying at least one X substituent wherein X is Cl, Br or I; and
(B) contacting cationically polymerizable monomers with the solution of activated catalyst of (A).

8 Claims, No Drawings

METHOD AND CATALYST FOR POLYMERIZING A CATIONIC POLYMERIZABLE MONOMER

BRIEF DESCRIPTION

This invention relates to the polymerization of alpha-olefins into fluids using novel stable catalyst solutions. Activated catalysts are prepared by admixing hydrocarbyl halide activators with aluminum trihalides, alkyl aluminum halides, or aluminum tralkyls at certain ratios, optionally in a suitable solvent. These stable activated catalyst solutions cause polymerization of monomers on contact without extended induction periods to produce polymeric fluids useful as lubricating oils, hydraulic fluids, heat exchanging liquids and the like having high viscosity and viscosity index values.

BACKGROUND OF THE INVENTION

The polymerization of alpha-olefins to product synthetic lubrcating oils with Friedel-Craft type cationic catalysts is well known. However, these catalysts or processes have certain restrictions, such as catalyst selection limited to soluble compounds, the need for longer and uncertain induction periods, or low conversion rates of the monomer.

U.S. Pat. No. 2,525,788 (Fontana et al.) discloses high viscosity oils made from alpha-olefins. The choice of the aluminum halide is limited to $AlBr_3$ because of its solubility in hydrocarbon solvents. Aluminum halides (e.g. $AlCl_3$) insoluble in such solvents cannot be used. The selection and use of promoters is in variance with the findings of the present invention.

U.S. Pat. No. 2,559,984 (Montgomery et al.) discloses the use of an insoluble aluminum chloride "sludge" by a batch or continuous process. Monomer conversion is limited to 10–20%, and only by repeated recycling is it possible to obtain high viscosity polymeric fluids. The catalysts of the instant invention are in solution and produce high viscosity polymer upon contact with the monomers.

U.S. Pat. No. 3,312,748 (Johnson) discloses the use of the reaction products of triorganoaluminum or organoaluminum halides with carbon tetrachloride or an alkyl haloform as catalyst to polymerize alpha-olefins. Aluminum trihalides are excluded as catalyst components. The formation of the active products which are insoluble or partially soluble precipitates requires uncertain or extended induction periods which may be reduced by heating to elevated temperatures or by the use of a second initiator, such as titanium tetrachloride.

U.S. Pat. No. 4,041,098 (Loveless) discloses a soluble catalyst system generated in situ by the addition of one solution of an alpha-olefin containing a soluble alkyl aluminum halide to a second solution of the olefin containing an organohalide initiator. The process is capable of producing fluids having high viscosity and viscosity index values and low pour points. However, it suffers form limiting the choice of catalysts to those soluble in the monomer.

SUMMARY OF THE INVENTION

The object of the present invention is to provide an improved method for the polymerization of cationically polymerizable monomers, and a catalyst solution useful for said polymerization.

The method to produce these catalysts comprises admixing (a) aluminum compounds of the general formula of $R_nAlX_{3-n}$, wherein R is $C_1$–$C_{12}$ alkyl, $C_6$–$C_{10}$ aryl; $C_7$–$C_9$ aralkyl or $C_7$–$C_{18}$ alkaryl; X is Cl, Br or I, and n is an integer from 0 to 3; and (b) a compound having the structure R'X wherein X has the meanings above, and R' is $C_1$–$C_{24}$ alkyl, $C_3$–$C_{20}$ alkenyl, $C_5$–$C_9$ bridged or nonbridged cyclyalkyl or cycloalkenyl, $C_7$–$C_9$ aralkyl or (b) is a hydrocarbon polymer carrying at least one X substituent wherein X has the meanings above. Said hydrocarbon polymer may be selected from the group consisting of poly(vinyl chloride), poly(vinylidene chloride), halogenated poly(alpha-olefins), halogenated polydienes, halogenated paraffins and halogenated naphthenic oils. The X substituent of the R'X activator should not be attached to a carbon atom carrying another X substituent.

Preferably, R is $C_1$–$C_{12}$ alkyl, benzyl, tolyl or xylyl, X is Cl or Br, and R' is linear or branched, primary, secondary or tertiary $C_2$–$C_{24}$ alkyl, allyl or benzyl. The R'/X weight ratio of the R'X activator may be from 9.5/1 to 1/8.1, preferably from 4.9/1 to 1/4.3. Typical examples for R are methyl, ethyl, propyl, butyl, hexyl, octyl, decyl, dodecyl, including linear or branched, primary or secondary alkyls, also phenyl, benzyl and the like. Suitable R'X activators are ethyl bromide, propyl iodide, ethylene bromide, t-butyl chloride, 1,2-dibromobutane, 2,3-dichloropentane, 1,2-diiodocyclohexane, benzyl chloride, 1, 2, 7, 8-tetrachlorooctane, 1,2-dibromodecane, hexachlorocyclopentadiene, chlorinated (30–70%, weight) polyethylene, chlorinated poly(alpha-olefins) and the like. Typical solvents are methylene chloride, chloroform, the freons, tetrachloroethylene, chlorobenzene, dichlorobenzene.

Cationically polymerizable monomers include $C_3$–$C_{14}$ linear or branched 1-olefins, such as propylene, isobutylene, 1-pentene, 1-octene, 2-ethyl-1-hexene, 1-decene, 1-dodecene, 2-butyl-1-octene, 1-tetradecene, as well as dienes such as butadiene, isoprene or mixtures of such monomers. It is advisable to base the selection of the hydrocarbyl halide solvents on the type of aluminum compound used. The halogen atoms of the trihalide should be equal or higher on the electronegativity scale than those of the solvent to prevent the occurrence of any interaction between the two. For example, chloroalkyls, such as methlene chloride and chloroform are best not used with aluminum bromide or iodides. It is preferable and advatageous to use solvents having densities higher than water for better protection of the catalyst solution from moisture.

The activity and efficiency of the activated catalyst in polymerizations are influenced to some degree by the compatibility of the solvent with the activated catalyst and the monomers. Thus, aside from the choice in the components of the catalyst pairs, the choice of solvents adds further to the versatility and use of the solution catalysts of this invention in the polymerization of the cationically polymerizable monomer. Said solvent may be toluene, xylene or a $C_1$–$C_{12}$ hydrocarbon have, F, Cl or Br as substituent and is essentially inert to a mixture of the above compounds of the formulae $R_nAlX_3$ and R'X as defined above. The solvent should bepresent in a sufficient amount to solubilize the activated catalyst. It is preferred that the solvent have a boiling point of at least 30° C.

The ratio of solvent to the mixture of catalyst and activator is from 1/99 to 95/5 and preferably from 75/25 to 90/10 by weight. Some of the advantages of this invention over the known processes may be summarized as (1) no limitations or restrictions imposed on the choice of the aluminum containing component of the catalyst with respect to type, (e.g., $R_2AlX$, $R_3Al$, $R_nAlX_{3-n}$, $AlX_3$), structure (e.g., R-alkyl or aryl or mixtures thereof, and X is Cl, Br or I), or solubility properties; (2) unlimited selection of activators with respect to the hydrocarbyl moiety and the halide, i.e., Cl, Br or I with the proviso that the halogen be capable of activating the aluminum catalyst commponent; and (3) broad selection of solvents, with the proviso that that they dissolve the activated catalyst without changing the catalyst's activity.

In the practice of this invention the polymeric hydrocarbon fluids are prepared by contacting one or more alpha-olefin monomers with a solution of activated catalyst prepared previously by reacting an aluminum trihalide, or an organo aluminum halide or an organo aluminum sesquihalide with a hydrocarbyl halide activator, possibly in a solvent so that the X/Al ratio is at least 3.1/1, preferably at least 4/1, most preferably 4/1-12/1, molar. It is to be understood that the activator may be used in excess to serve as solvent for the activated catalyst or if necessary, a solvent other than an activator may be added for salvation purposes, especially where the activator is a compound being non-liquid at reaction temperature. To perform the invention conveniently, the catalyst solution and the monomer which can be in the neat or solution are charged into a stirred flask or autoclave or a pipe reactor. The reaction to form the polymer is very rapid and hence easily adaptable to a continuous polymerization process. This is achieved by removal of the reaction mixture at the rates that the reactants are introduced. It is necessary at times to adjust "residence time" to achieve optimum viscosities or other product properties and this can be easily done by adjusting the rates of in- and out-flow of the reactants and the product. A means for cooling the reactor is advisable in order to control the polymerization temperature between 0°–200° C., preferably between 10°–80° C. Polymer viscosities are inversely related to reaction temperatures. Higher temperatures yield lower viscosities, and lower temperatures yield higher viscosities. Thus reaction temperature, and "residence time" combined can be very effective variables in controlling the viscosity of the reaction mixture and of the product.

After the completion of the polymerization, the crude product is "quenched" by a low molecular weight alcohol or a dilute solution of an alkali metal aloxide in the alcohol followed by the removal of the precipitate via filtration and/or water wash or another suitable process, such as centrifugation. The product may be isolated by removal of solvents and low boiling oligomers (e.g., dimers, etc.) with distillation under heat and vacuum. The resultant polymeric oils have superior oxidative resistance and trace residual halogen content (usually less than 0.05%).

In the practice of this invention, as is common with any organometallic catalyst, all reactants and equipment should be substantially free from moisture and/or air and reactive materials. Monomers and solvents are dried with desiccants, e.g., molecular sieves and anhydrous metal salts. The reaction vessel and the related equipment are conveniently dried by heat and/or dry inert gas purge. The activated catalyst solution in volatile halocarbon solvents, such as methylene chloride and chloroform, if well shielded from moisture, are stable and active for extended periods of time.

The catalyst levels operable in this invention range from 0.1 to 5.0 percent by weight of the total monomer. The catalyst weight is calculated on the basis of the aluminum compound, and the activator weight is adjusted accordingly to provide the mole ratio of halogen to aluminum (X/Al) or at least 3.1. Higher levels of activators, i.e., at X/Al ratios higher than 4 may be employed, but little is to be gained by use of higher levels of catalyst even though there is no upper limit.

The temperature operable in the practice of this invention normally ranges from 0° to 200° C. although temperatures outside this range may be used. Preferably a polymerization temperature from 10°–80° C. can be used. For example, temperatures much below zero can be employed, but increased levels of catalyst become necessary for achieving satisfactory monomer conversion.

The present invention is further described by the examples below in order to illustrate the invention without limiting its scope.

EXAMPLE #1

This example illustrates the preparation of an oligomer of decene-1 utilizing a solution catalyst prefared from aluminum trichloride and a liquid $C_{24}$ chlorohydrocarbon wax containing 30% by weight of chlorine, in methylene chloride.

The solution catalyst was prepared in advance by placing 1.48 g of reagent grade $AlCl_3$ in a dry, nitrogen purged 250 ml Erlenmeyer flask fitted with a 3-hole rubber stopper. Two of the holes served as the inlet-outlet pathway for the dry nitrogen gas, and the third as the porthole for the introduction and removal of liquids by a syringe. A volume of 50 ml methylene chloride was introduced to the flask which, after swirling for a period of time, failed to dissolve the halide to any visible extent other than to produce a light green tint of color. To this mixture 0.90 ml of the initiator was added dropwise. A brownish color developed with every drop which faded until sufficient amount of the initiator was added to prevent the fading. On completion, a deep burgundy red solution resulted which contained some residual insoluble powder amounting to 1% or less of the $AlCl_3$ present. (While it was not necessary to cool the reaction flask here, it is advisable to do so: particularly with aluminum compounds with lower alkyl groups the reactions may be vigorous, possibly causing rapid escape of monomers and/or solvent.)

The polymerization reaction in this, as well as in the later examples which follow, are performed in a dry, nitrogen filled, 4-necked, 500 ml round bottomed flask which was fitted with:

(1) a thermometer;
(2) an overhead mechanical motor attached to a glass shaft stirrer with a teflon stirring blade;
(3) 125 ml and 250 ml dropping funnels having pressure equalizing side arms, and metering teflon stopcocks. Both were fitted with gas inlet adapters for purging and maintaining positive nitrogen pressure; and
(4) a pan containing cold water on top of a jack was placed under the reaction flask to permit cooling when needed.

The previously prepared activated catalyst solution in methylene chloride was syringed into one of the dropping funnels (A), and the transfer made quantitative by multiple rinsings of the flask and transfers to the funnel. The volume in the funnel was brought to 72 ml mark with addition of the solvent.

In the second funnel (B) was syringed 200 ml (148 g) dry decene-1, and the polymerization started by adding simultaneously the contents of the two funnels. Funnel (A) was metered to deliver 0.80 ml/min. of solution, and funnel (B) 2.2 ml/min. of monomer so that the entire contents of the funnel were added within 90 minutes. The polymerization reaction started immediately and was observable by the formation of a light greenish tinted viscous oil. The reaction was exothermic throughout the addition of the reactants. The temperature was kept at 20°±2° C. during the period of addition. After the completion of addition (infrared analysis showed the monomer essentially all converted), the reaction mixture was stirred with 5 ml of methanol, and the precipitate formed was removed by filtering the slurry through a bed of celite filter aid (Fisher Scientific Co.) under reduced pressure. The clear crude product was distilled first under moderate vacuum to remove low boiling solvent, residual monomer or dimer, and then under a high vacuum of 0.1 mm Hg and a pot temperature of 250°-270° C. Usually a head temperature of up to 170° C. is observed. The undistilled vicsous liquid residue is the final product with a yield of 93% of the theoretical value. The product of the current example was clear, pale yellow oil having a kinematic viscosity of 43 cSt at 100° C., 411 cSt at 40° C. and a viscosity index (V.I.) of 158 and contained less than 0.05% Cl.

EXAMPLE #2

The polymerization and the work-up procedures were essentially the same as Example #1, except that the aluminum compound used was ethylaluminum sesquichloride (EASC), 8.0 ml of 25% solution in hexane equivalent to 1.5 g, plus 2.5 ml (2.24 g) of the $C_{24}$ chlorohydrocarbon sufficient to provide Cl/Al molar ratio of four. The catalyst solution was prepared in methylene chloride. The reaction flask was cooled in ice water to moderate the exothermic reaction. As the weight of the added chlorohydrocarbon became sufficient to form a 3:1 Cl/Al ratio, solid $AlCl_3$ started to precipitate out. As this ratio was increased to 4:1 with continued addition of the chlorohydrocarbon the precipitate re-dissolved to form a clear burgundy red solution.

The final product (produced in 94% yield) had a kinematic viscosity at 100° C. ($KV_{100}$) of 41.9 cSt, a $KV_{40}$ of 400 cSt, V.I. of 157 and less than 0.05% Cl. The product viscosities of Examples #1 and #2 show no significant difference.

EXAMPLE #3

The procedure of Example #1 essentially followed (% catalyst, temperature, and time) except that the aluminum containing component utilized in the catalyst was diethyl aluminum chloride (DEAC).

The product (95% yield) had $KV_{100}$ of 40.6 cSt, $KV_{40}=379$, and V.I. of 158, and less than 0.05% Cl, which represent values essentially the same as those in Examples #1 and #2.

EXAMPLE #4

This example is essentially the same as the previous three examples above, except the aluminum containing catalyst component was triethyl aluminum (TEA). The preparation of the activated catalyst solution was modifed by adding the chlorohydrocarbon activator to the solution of TEA in hexane causing precipitation of the activated catalyst. The precipitate dissolved when $CH_2Cl_2$ was added forming a clear burgundy colored catalyst solution.

The product (94% yield) had a $KV_{100}$ or 40.2 cSt, $KV_{40}$ of 378, and V.I. of 157 and less than 0.05% Cl.

EXAMPLE #5

This example illustrates that higher catalyst concentration increases polymer molecular weight as indicated by viscosity. The polymerization was carried out following essentially the procedure of Example #1 except 2.96 g (or 2%) of $AlCl_3$ and 1.8 ml (or 1.6 g) $C_{24}$ halohydrocarbon were used. The product (93% yield) had a $KV_{100}$ of 50 cSt, $KV_{40}$ of 502 cSt, and a V.I. of 158 and less than 0.05% Cl.

EXAMPLE #6

This example shows the effect of different halogen atoms, e.g., Cl vs. Br, on the viscosity of the polymer produced. Two polymers produced under substantially the same reaction conditions are compared below:

| Catalyst/Activ./Solv. | Wt % | X/Al (Molar) | Tmp. (°C.) | Yield (g) | $KV_{100}$ (cSt) | $KV_{40}$ (cSt) | V.I. |
| --- | --- | --- | --- | --- | --- | --- | --- |
| $AlBr_3$/t-BuBr/$MeBr_2$ | 1 | 4:1 | 20 | 98 | 76 | 913 | 160 |
| $AlCl_3$/t-BuCl/$MeCl_2$ | 1 | 4:1 | 20 | 92 | 43 | 330 | 158 |

The data indicate that, everything being equal, the use of Br increases the viscosity of the product obtained. The use of $MeBr_2$ with $AlBr_3$ was necessary since $MeCl_2$ would exchange Cl atoms for Br atoms on the aluminum compound. Both polymers contain less 0.05% halogen.

EXAMPLE #7

Experiments were conducted following essentially the procedure of Example #1 demonstrating the effect of different organohalide activators, i.e., 2,3-dibromobutane (DBB) vs. tert-butyl bromide (TBB).

The data are summarized below.

| Catalyst/Init./Solv. | Solv (ml) | Wt % | X/Al (Molar) | Tmp. (°C.) | Yield (g) | $KV_{100}$ (cSt) | $KV_{40}$ (cSt) | V.I. |
| --- | --- | --- | --- | --- | --- | --- | --- | --- |
| $AlBr_3$/DBB/$MeBr_2$ | 50 | 2 | 4:1 | 20 | 99 | 55 | 592 | 156 |
| $AlBr_3$/TBB/$MeBr_2$ | 50 | 1 | 4:1 | 20 | 99 | 76 | 913 | 160 |

The data indicate that DBB produces a product of lower viscosity, even when used at twice the level of that of T-BB. The halogen content of both products was less than 0.05%.

EXAMPLE #8

The example describes two modified methods for a batch polymerization of monomers by the solution catalysts of this invention. The apparatus required by the two methods here is the same as in Example #1, except that only one addition funnel is used.

In method (A) all the monomer is charged to the reaction flask, and the catalyst solution added from the funnel at a rate to maintain a given reaction temperature; and in method (B), which is preferable, the addition sequence is reversed, i.e., all the catalyst solution is charged to the reaction flask and the monomer added from the funnel, and again, at a rate to maintain a given reaction temperature.

Two polymers of decene-1 were produced with the results summarized below:

| Catalyst/Activator/Solv. | Method | EASC[1] (g) | CWX-LV[2] (ml) | MeCl$_2$ (ml) | Decene-1 (ml) | Tmp. (°C.) | Yield (g) | KV$_{100}$ (cSt) | KV$_{40}$ (cSt) | V.I. |
|---|---|---|---|---|---|---|---|---|---|---|
| EASC/CWX-LV/MeCl$_2$ | A | 5.5 | 1.58 | 26 | 200 | 0–5 | 99 | 39.6 | 366 | 158 |
| EASC/CWX-LV/MeCl$_2$ | B | 16 | 5.0 | 36 | 200 | 0–5 | 99 | 54.5 | 566 | 160 |

[1] Ethylaluminum sesquichloride, 25 wt % solution in hexane;
[2] Chlorowax-LV [trademark] a C$_{24}$ chlorohydrocarbon containing 30 wt % chlorine, total halogen content less than 0.05% in each case.

The Method (B) is principally safe, and the preferred method to use because the mass of the polymerizing monomer in the flask is controlled by the addition rate from the funnel. It permits better control.

The Method (A) may be potentially hazardous, especially for large scale polymerization because of a small amount of catalyst added to the body of the monomer which could trigger a very rapid and exothermic reaction which would be difficult to control.

What is claimed is:

1. A process for polymerizing cationically polymerizable monomers comprising:
   (A) providing a solution containing an activated catalyst comprising
      (a) an aluminum compound having the formula $R_nAlX_{3-n}$ wherein n is an integer from 0 to 3; R is $C_1$–$C_{12}$ alkyl, $C_7$–$C_8$ aralkyl, $C_7$–$C_{18}$ alkaryl or $C_6$–$C_{10}$ aryl; and X is Cl, Br or I; and
      (b) (1) a compound having the formula R'X, which is reactive with (a), wherein X is Cl, Br or I and R' is $C_1$–$C_{24}$ alkyl, $C_3$–$C_{20}$ alkenyl, $C_5$–$C_9$ bridged or non-bridged cycloalkyl or cycloalkenyl, $C_7$–$C_9$ aralkyl or (2) a hydrocarbon polymer carrying at least one X substituent wherein X is Cl, Br or I; and
      (c) a solvent selected from the group consisting of toluene, xylene or $C_1$–$C_{12}$ hydrocarbon having F, Cl or Br substituents, said solvent being essentially inert to the mixture of (a) and (b), said solvent being present in an amount sufficient to solubilize the activated catalyst; and
   (B) contacting cationically polymerizable monomers with the solution of activated catalyst of (A).

2. The process of claim 1 wherein said hydrocarbon polymer is selected from the group consisting of poly(vinyl chloride), poly(vinylidene chloride), halogenated poly(alpha-olefins), halogenated polydienes, halogenated paraffins and halogenated naphthenic oils.

3. The process of claim 1 wherein the overall X/Al molar ratio of (a) plus (b) is at least 3:1/1.

4. The process of claim 1 wherein said solvent has a boiling point of at least 30° C.

5. The process of claim 3 wherein said X/Al ratio is at least 4/1 molar.

6. The process of claim 1 wherein the R'/X weight ratio of the activator R'X of (b) is from 9.5/1 to 1/8.1.

7. The process of claim 1 wherein the polymerization temperature is 0°–200° C.

8. The process of claim 7 wherein the polymerization temperature is 10°–80° C.

* * * * *